United States Patent [19]

Iwahara

[11] Patent Number: 4,769,501

[45] Date of Patent: Sep. 6, 1988

[54] PROCESS FOR PRODUCING ALKYLPHENOLS

[75] Inventor: Masahiro Iwahara, Tokuyama, Japan

[73] Assignee: Idemitsu Petrochemical Co., Ltd., Tokyo, Japan

[21] Appl. No.: 75,948

[22] Filed: Jul. 21, 1987

[51] Int. Cl.$^4$ .................... C07C 37/20; C07C 37/00
[52] U.S. Cl. .................... 568/799; 568/716; 568/727
[58] Field of Search ............ 568/716, 727, 728, 766, 568/780, 784, 790, 799

[56] References Cited

U.S. PATENT DOCUMENTS

| | | | |
|---|---|---|---|
| 2,841,624 | 7/1958 | Norton et al. | 568/784 |
| 4,451,676 | 5/1984 | Everly | 568/781 |
| 4,475,001 | 10/1984 | Leston | 568/784 |
| 4,633,022 | 12/1986 | Greco | 568/780 |

*Primary Examiner*—Werren B. Lone
*Attorney, Agent, or Firm*—Antonelli, Terry & Wands

[57] ABSTRACT

There is disclosed a process for producing an alkylphenol comprising reacting a phenol with an aldehyde and hydrogen in the presence of (a) an alkaline or alkaline earth metal catalyst selected from a hydroxide of an alkaline metal, hydroxide of an alkaline earth metal, a carbonate of an alkaline metal, and a hydrogencarbonate of an alkaline metal and (b) a hydrogenation catalyst. By the use of the process, the alkylphenols can be produced in good yield in one stage method.

18 Claims, No Drawings

PROCESS FOR PRODUCING ALKYLPHENOLS

BACKGROUND OF THE INVENTION (1) Field of the Invention

The present invention relates to a process for producing alkylphenols and, more particularly, it relates to a process for producing alkylphenols in good yield using one stage method.

(2) Description of the Prior Art

A two stage method for producing alkylphenols which are useful as antioxidants and materials of other chemical products is disclosed in U.S. Pat. No. 2,909,568. The method comprises reacting a phenol with formaldehyde in the presence of a basic catalyst to form a (hydroxymethyl)phenol followed by reduction with hydrogen to form a methylphenol.

However, the above described method is complicated in practice since it needs acid precipitation of the (hydroxymethyl)phenol which is recovered as a salt thereof in first stage. Further, at relatively low temperature, the first stage should be carried out for very long time and, in such a condition, the yield of the (hydroxymethyl)phenol is low, resulting in a low yield of the methylphenol.

SUMMARY OF THE INVENTION

The object of the present invention is to produce alkylphenols by a one stage method in good yield.

It has been found, as the result of diligent study, that alkylphenols can be produced in good yield in one stage by reacting a phenol with an aldehyde and hydrogen in the presence of certain catalysts, and the knowledge led them to complete the invention.

The present invention is a process for producing an alkylphenol comprising reacting a phenol with an aldehyde and hydrogen in the presence of (a) an alkaline or alkaline earth metal catalyst selected from an hydroxide of an alkaline metal, an hydroxide of an alkaline earth metal, carbonate of an alkaline metal, and a hydrogencarbonate of an alkaline metal and (b) a hydrogenation catalyst.

DETAILED DESCRIPTION OF THE INVENTION

The phenols which may be used in the process of the present invention are those represented by the general formula

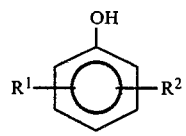

wherein each $R^1$ and $R^2$ is independently selected from alkyl radicals and alkoxy radicals. The illustrative examples of such phenol include phenol, o-cresol, m-cresol, p-cresol, xylenol, ethylphenol, propylphenol, p-tert-butylphenol, p-tert-amylphenol, o-sec-amylphenol, octylphenol, nonylphenol, 2,6-dimethylphenol, 2,6-diethylphenol, 2,6-diisopropylphenol, 2,6-di-tert-butylphenol, 2,6-di-tert-amylphenol, 2,6-di-sec-amylphenol. Among these, 2,6-di-tert-butylphenol is preferably used.

The aldehydes which may be used in the process of the present invention are those represented by the general formula $R^2CHO$ wherein $R^3$ is selected from hydrogen and alkyl radicals.

The illustrative examples of such aldehyde include formaldehyde, acetaldehyde, propionaldehyde, enanthaldehyde, acrolein, crotonaldehyde, hydroxy-aldehyde, salicylaldehyde, anisaldehyde, vanillin. Among these, formaldehyde is preferably used. Formaldehyde may be used in the form of monomer, and may also be used in the form of trioxane, paraformaldehyde, or the like, which liberates formaldehyde under the reaction condition. Alternatively, it may be used as an aqueous solution (formalin).

The above described hydrogen may includes impurities in some quantity so long as the forming of the alkylphenols is not to be disturbed, and for example, those obtained by conversion of water gas, gasification of petroleum, complete gasification of coal, conversion of natural gas may be used.

The above described phenols and aldehydes react as shown, for example, in the following equation to form the corresponding alkylphenols.

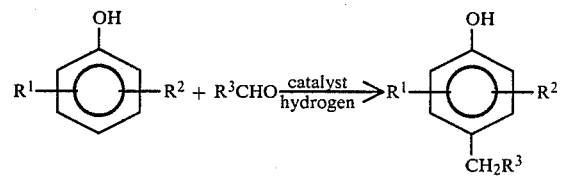

The reaction in the process of the present invention is conducted in the presence of an alkaline or alkaline earth metal catalyst selected from a hydroxide of an alkaline metal, a hydroxide of an alkaline earth metal, a carbonate of an alkaline metal, and a hydrogencarbonate of an alkaline metal. The illustrative examples of the hydroxide of alkaline or alkaline earth metal include sodium hydroxide, potassium hydroxide, lithium hydroxide, magnesium hydroxide, calcium hydroxide, barium hydroxide. The illustrative examples of the carbonate or hydrogencarbonate of alkaline metal include lithium carbonate, lithium hydrogencarbonate, sodium carbonate, sodium hydrogencarbonate, potassium carbonate, potassium hydrogencarbonate, rubidium carbonate, rubidium hydrogencarbonate, cesium carbonate, cesium hydrogencarbonate, francium carbonate, francium hydrogencarbonate, sodium-potassium carbonate. These may be used individually or in a combination of two or more of them, and the amount to be used of these, which is not to be particularly limited, is usually 1/300 to 1/10 mol, preferably 1/200 to 1/50 mol per 1 mol of the phenol.

The reaction in the process of the present invention which is carried out by contacting a phenol, an aldehyde, and hydrogen in the presence of the above described catalyst also needs the presence of a hydrogenation catalyst. The illustrative examples of the hydrogenation catalyst to be used in the process of the present invention include nickel or cobalt catalysts such as nickel sulfide catalyst, nickel sulfide catalyst, nickel peroxide catalyst, nickel-pumice catalyst, nickel-thioria-diatomaceous earth catalyst, nickel-copper-alumina catalyst, nickel-diatomaceous earth catalyst, nickel-alumina catalyst, nickel-berillia catalyst, nickel-chromia catalyst, nickel chromite catalyst, nickel-calcium phosphate catalyst, Raney nickel catalyst, Urushibar nickel catalyst, nickel formate catalyst, cobalt-diacetomaceous earth catalyst, cobalt-copper catalyst, cobalt-barium oxide-alumina catalyst, cobalt-molybdenum catalyst, cobalt-thoria-magnesia-ciatomaceous earth catalyst, cobalt-thoria-magnesia-diacetomaceous earth catalyst, Raney-cobalt-catalyst, Urushibara-cobalt catalyst, and cobalt formate catalyst; chromium catalysts such as chromium oxide catalyst and chromium oxide catalyst supported on a carrier; molybdenum or tungsten catalysts such as Raney tungsten catalyst, molybdenum oxide catalyst, molybdenum oxide catalyst supported on a carrier, tungsten disulfide catalyst, molybdenum trisulfide catalyst, tungsten disulfide catalyst, molybdenum chloride catalyst, molybdenum pentachloride catalyst, and tungsten chloride catalyst; platinum group catalysts such as ruthenium chloride catalyst, ammonium chlororuthenate catalyst, ruthenium hydroxide catalyst, ruthenium dioxide catalyst, potassium ruthenate catalyst, ruthenium-carbon catalyst, ruthenium catalysts supported on a carrier, colloidal rhodium catalyst, rhodium oxide catalyst, rhodium hydroxide catalyst, rhodium chloride catalyst, sodium chlororhodate catalyst, ammonium chlororhodate catalyst, rhodium catalysts supported on a carrier, palladium chloride catalyst, chlorotetraammine palladium catalyst, ammonium tetrachloropalladate catalyst, palladium oxide catalyst, palladium hydroxide catalyst, palladium black catalyst, colloidal palladium catalyst, palladium-carbon catalyst, palladium hydroxide-carbon catalyst, palladium-barium sulfate catalyst, palladium-calcium carbonate catalyst, other palladium catalysts supported on a carrier, osmium black catalyst, colloidal osmium catalyst, osmium-carbon catalyst, osmium-alumina catalyst, iridium black catalyst, colloidal iridium catalyst, iridium oxide catalyst, iridium oxide-platinum oxide catalyst, iridium asbestos catalyst, iridium-carbon catalyst, platinum black catalyst, colloidal platinum catalyst, platinum-carbon catalyst, platinum-asbestos catalyst, platinum-silica gel catalyst, and platinum-alumina catalyst. Among these, the preferred are platinum group catalysts, and particularly preferred are palladium-carbon catalyst and platinum-carbon catalyst. The amount to be used, which is not to be particularly limited, is usually 1 to 80 g, preferably 5 to 50 g for 1 mol of phenol.

In conducting the reaction, a solvent, for example alcohols such as methanol, ethanol, isopropanol, tert-butanol, etc. and ethers such as diethyl ether, methyl ethyl ether, tetrahydrofuran, 1,4-dioxane, etc., may be optionally used.

The ratio of the phenol and the aldehyde, which is not to be particularly limited, is usually 1 to 6 mol, preferably 2 to 4 mol of aldehyde to 1 mol of phenol.

The reaction pressure, which is not to be particularly limited, is usually 0 to 10 kg/cm$^2$-G, preferably 0 to 70 kg/cm$^2$-G, and it is desirable to control the conditions so that the partial pressure of hydrogen is in the range of from 1 to 95 kg/cm$^2$-G, preferably from 1 to 90 kg/cm$^2$-G.

The reaction temperature, which is not to be particularly limited, is usually 50° to 150° C., preferably 70° to 130° C., and the reaction time is usually 1 to 20 hours, preferably 2 to 10 hours.

The reaction in the process of the present invention may either be carried out in a batch type reaction or be carried out using the catalyst in a continuous-flow system such as fixed bed, fluidized bed, or the like.

According to the present invention, alkylphenols can be produced from a phenol and an aldehyde by one stage reaction in good yield and therefore, the industrial value of the present invention is extremely large.

The alkylphenols produced according to the present invention are useful as antioxidants, raw materials of other chemical products, and the like.

EXAMPLES AND COMPARATIVE EXAMPLES

The present invention will now be described in details with reference to the following Examples that by no means limit the scope of the invention.

EXAMPLES 1 TO 4

Into a 50-ml autoclave were charged a phenol, an aldehyde, an alkaline or alkaline earth metal catalyst, hydrogenation catalyst, and a solvent listed in the Table in the quantities listed in the Table. Hydrogen was introduced into the autoclave and reaction was carried out under the conditions shown in Table. After the conclusion of the reaction, the content was cooled to 25° C., the reaction product was filtered, and the filtrate was analyzed by gas chromatography. The yield of the alkylphenol was calculated on the basis of the amount of the phenol.

EXAMPLES 5 TO 12

The procedure of Examples 1 to 4 was repeated with the exception that a 250-ml autoclave was used in place of the 50-ml autoclave.

COMPARATIVE EXAMPLE 1

310 g of 2,6-dimethoxyphenol, 300 g of 38 wt% formalin, and 810 g of 10% wt% aqueous sodium hydroxide were reacted for 60 hours at 25° C. under a pressure of 0 kg/cm$^2$-G, the reaction mixture was and then neutralized with sulfuric acid, to obtain 80 g of 2,6-dimethoxy-4-(hydroxymethyl)phenol. (Yield: 22 mol%) 25 g of the obtained 2,6-dimethoxy-4-(hydroxymethyl)-phenol was reacted in 320 ml of methanol in the presence of 0.375 wt% of platinum-alumina catalyst and hydrogen for 4 hours at 200° C. at 199 kg/cm$^2$-G, and 15 g of 2,6-dimethoxy-4-methylphenol was obtained. (Yield: 66 mol%) The yield on the basis of the amount of the raw material was 15 mol%.

COMPARATIVE EXAMPLE 2

108 g of o-cresol, 215 g of 38 wt% formalin, 50 g of sodium hydroxide, and 200 g of water were reacted for 96 hours at 25° C., and the reaction mixture was then neutralized with acetic acid, to obtain 126 g of 2,6-bis(-hydroxymethyl)-4-methylphenol. (Yield: 75 mol%) The obtained 2,6-bis(hydroxymethyl)-4-methylphenol was reacted in 250 ml of methanol in the presence of 0.375 wt% of platinum-alumina catalyst and hydrogen for 4 hours at 180° C. at 179 kg/cm$^2$-G, and 15 g of 2,4,6-trimethylphenol was obtained. (Yield: 45 mol%) The yield on the basis of the raw material was 34 mol%.

TABLE

| | | Example | | | | | | | | | | | |
|---|---|---|---|---|---|---|---|---|---|---|---|---|
| | | 1 | 2 | 3 | 4 | 5 | 6 | 7 | 8 | 9 | 10 | 11 | 12 |
| Phenolic compound (mmol) | 2,6-di-tert-butylphenol | 8 | 8 | 8 | 8 | 120 | 120 | 120 | 120 | 120 | 120 | 120 | 120 |

TABLE-continued

| | | Example | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Aldehyde (mmol) | 35 wt % formalin | 20 | 20 | — | 20 | 200 | — | — | — | 200 | — | — | — |
| | 92 wt % paraformaldehyde | — | — | 20 | — | — | 200 | 200 | 200 | — | 200 | 200 | 200 |
| Alkline/alkaline earth metal catalyst | sodium hydroxide | — | 0.05 | — | — | | | | | | | | |
| | lithium hydroxide | 0.05 | — | 0.05 | 0.05 | | | | | | | | |
| | sodium carbonate | | | | | 1 | 1 | — | — | — | — | — | — |
| EX. 1–4(mmol) | sodium hydrogencarbonate | | | | | — | — | 0.5 | — | — | — | — | — |
| EX. 5–12(g) | patassium carbonate | | | | | — | — | — | 0.5 | 0.5 | 0.5 | 0.5 | 0.5 |
| Hydrogenation catalyst (mg) | 5 wt % palladium supported on carbon | 200 | 200 | — | 200 | 500 | 500 | 500 | 500 | 500 | — | 500 | 500 |
| | 5 wt % palladium supported on alumina | — | — | 400 | — | — | — | — | — | — | — | — | — |
| | 5 wt % platinum supported on carbon | — | — | — | — | — | — | — | — | — | 500 | — | — |
| Solvent (ml) | methanol | 20 | 20 | 20 | 20 | 100 | 100 | 100 | 100 | 110 | 100 | 100 | 100 |
| Temperature (°C.) | | 90 | 90 | 90 | 90 | 130 | 130 | 130 | 110 | 120 | 120 | 110 | 110 |
| Pressure (kg/cm-G) | | 7 | 7 | 7 | 7 | 20 | 20 | 20 | 20 | 20 | 20 | 20 | 20 |
| Time (hour) | | 5 | 5 | 5 | 5 | 5 | 5 | 5 | 4 | 5 | 6 | 4 | 4 |
| Yield of alkylphenol (mol %) | 2,6-di-tert-butyl-4-methylphenol | 84.0 | 63.5 | 78.0 | 59.2 | 80 | 85 | 83 | 94 | 82 | 65 | 93 *1 | 91 *2 |

*1 The hydrogenation catalyst employed in Ex. 4 was reused. (the second time)
*2 The hydrogenation catalyst employed in Ex. 4 was reused. (the third time)

What is claimed is:

1. A process for producing an alkylphenol comprising reacting a phenol selected from the group consisting of o-cresol,, m-cresol, p-cresol, xylenol, ethylphenol, propylphenol, p-tert-butylphenol, p-tert-amylphenol, o-sec-amylphenol, octylphenol, nonylphenol, 2,6-methylphenol, 2,6-diethylephenol, 2,6-diisopropylphenol, 2,6-di-tert-butylphenol, 2,6-di-tert-amylphenol and 2,6-di-sec-amylphenol and with an aldehyde selected from the group consisting of formaldehyde, acetaldehyde, propionaldehyde, enanthaldehyde, acrolein, crotonaldehyde, hydroxy-aldehyde, salicylaldehyde, anisoaldehyde and vanillin and hydrogen in the presence of (a) an alkaline metal or alkaline earth metal catalyst selected from the group consisting of a hydroxide of an alkaline metal, a hydroxide of an alkaline earth metal, a carbonate of an alkaline metal, and a hydrogen carbonate of an alkaline metal and (b) a hydrogenation catalyst at a temperature of from 70° to 130° C. and at a hydrogen partial pressure of from 1 kg/cm$^2$-G to 95 kg/cm$^2$-G and with the ratio of the aldehyde to the phenol being from 1 to 6 mol of aldehyde per 1 mol of phenol.

2. The process of claim 1 wherein the phenol is 2,6-di-tert-butylphenol.

3. The process of claim 1 wherein the aldehyde is formaldehyde.

4. The process of claim 1 wherein the phenol is 2,6-di-tert-butylphenol, the aldehyde is formaldehyde, and the produced alkylphenol is 2,6-di-tert-butyl-4-methylphenol.

5. The process of claim 1 wherein the hydroxide of an alkaline metal is lithium hydroxide.

6. The process of claim 1 wherein the hydroxide of an alkaline metal is sodium hydroxide.

7. The process of claim 1 wherein the carbonate of an alkaline metal is sodium carbonate or potassium carbonate.

8. The process of claim 1 wherein the hydrogencarbonate of an alkaline metal is sodium hydrogencarbonate.

9. The process of claim 1 wherein the hydrogenation catalyst is palladium supported on carbon or platinum supported on carbon.

10. The process of claim 1 wherein the hydrogenation catalyst is palladium supported on alumina.

11. The process of claim 1 wherein the phenol is reacted with the aldehyde and hydrogen in the presence of (a) the alkaline metal or alkaline earth metal catalyst and (b) a hydrogenation catalyst selected from the group consisting of platinum supported on carbon, palladium supported on carbon and palladium supported on aluminum.

12. The process of claim 1 wherein the amount of alkaline metal or alkaline earth metal catalyst is from 1/300 to 1/10 molper mol of the phenol and the amount of the hydrogenation catalyst is from 1 to 80 g per mol of the phenol.

13. A process for producing 2,6-di-tert-butyl-4-methylphenol comprising reacting 2,6-di-tert-butylphenol with formaldehyde and hydrogen in the presence of (a) an alkaline metal catalyst selected from lithium hydroxide, sodium hydroxide, sodium carbonate, potassium carbonate, and sodium hydrogencarbonate and (b) a hydrogenation catalyst.

14. The process of claim 13 wherein the hydrogenation catalyst is palladium supported on carbon or platinum supported on carbon.

15. The process of claim 13 wherein the hydrogenation catalyst is palladium supported on alumina.

16. The process of claim 13 wherein 2,6-di-tert-butylphenol is reacted with formaldehyde and hydrogen in the presence of said (a) alkaline metal catalyst and said (b) hydrogenation catalyst at a temperature of from 70° C. to 130° C. at a hydrogen partial pressure of from 1 kg/cm$^2$-G to 95 kg/cm$^2$-G.

17. The process of claim 13 wherein the amount of alkaline metal or alkaline earth metal catalyst is from 1/300 to 1/10 mol per mol of the phenol and the amount of the hydrogenation catalyst is from 1 to 80 g per mol of the phenol.

18. The process of claim 17 wherein the ratio of the aldehyde to phenol is from 1 to 6 mol of aldehyde per 1 mol of phenol.

* * * * *

UNITED STATES PATENT AND TRADEMARK OFFICE
CERTIFICATE OF CORRECTION

PATENT NO. : 4,769,501

DATED : September 6, 1988

INVENTOR(S) : M. IWAHARA

It is certified that error appears in the above-identified patent and that said Letters Patent is hereby corrected as shown below:

Title page, left-hand column, please add the following after "[22] Filed: Jul. 21, 1987"

```
--[30]          Foreign Application Priority Data
    Jul. 22, 1986 [JP]      Japan..................61-170798
    Nov. 17, 1986 [JP]      Japan..................61-273434--
```

Signed and Sealed this

Twenty-eighth Day of February, 1989

Attest:

DONALD J. QUIGG

*Attesting Officer*    *Commissioner of Patents and Trademarks*